United States Patent
Manfredi et al.

(10) Patent No.: US 10,371,128 B2
(45) Date of Patent: Aug. 6, 2019

(54) COMPLIANT ACTUATOR

(71) Applicant: University of Dundee, Dundee (GB)

(72) Inventors: Luigi Manfredi, Dundee (GB); Alfred Cuschieri, Fife (GB)

(73) Assignee: UNIVERSITY OF DUNDEE, Dundee (GB)

(*) Notice: Subject to any disclaimer, the term of this patent is extended or adjusted under 35 U.S.C. 154(b) by 259 days.

(21) Appl. No.: 15/307,730

(22) PCT Filed: Apr. 23, 2015

(86) PCT No.: PCT/GB2015/051191
§ 371 (c)(1),
(2) Date: Oct. 28, 2016

(87) PCT Pub. No.: WO2015/166214
PCT Pub. Date: Nov. 5, 2015

(65) Prior Publication Data
US 2017/0051729 A1    Feb. 23, 2017

(30) Foreign Application Priority Data
Apr. 29, 2014  (GB) .................................. 1407490.0

(51) Int. Cl.
*B25J 17/00*   (2006.01)
*B25J 17/02*   (2006.01)
(Continued)

(52) U.S. Cl.
CPC ............ *F03G 7/065* (2013.01); *A61B 1/0055* (2013.01); *A61B 1/0057* (2013.01);
(Continued)

(58) Field of Classification Search
CPC .................. F03G 7/065; A61B 1/0058; A61M 2205/0266; B25J 9/1085
See application file for complete search history.

(56) References Cited

U.S. PATENT DOCUMENTS 5,556,370 A   7/1996 Maynard
6,374,608 B1  4/2002 Corris et al.
(Continued)

FOREIGN PATENT DOCUMENTS

DE   10 2012 211 499 A1   1/2013
EP       2 072 001 A2      6/2009
(Continued)

OTHER PUBLICATIONS

International Search Report and Written Opinion for corresponding PCT Application No. PCT/GB2015/051191; dated Jun. 1, 2015.
(Continued)

*Primary Examiner* — Jake Cook
(74) *Attorney, Agent, or Firm* — Tarolli, Sundheim, Covell & Tummino LLP (57) ABSTRACT

An actuator (12) includes a moving member (18) pivotally connected to a base unit (14) for rotation about an axis. The driving force for rotation of the moving member (18) relative to the base unit (14) is provided by a pair of antagonistically operating shape memory alloy (SMA) wires (48, 50) and transmitted via a torsional spring (56). An endoscope, or a snake-like robot (66), may include one or more of the actuators (12).

30 Claims, 12 Drawing Sheets

(51) Int. Cl.
  *B25J 18/00*    (2006.01)
  *F03G 7/06*    (2006.01)
  *A61B 1/005*    (2006.01)
  *A61B 34/30*    (2016.01)
(52) U.S. Cl.
  CPC ............ *A61B 1/0058* (2013.01); *A61B 34/30* (2016.02); *A61B 2034/301* (2016.02); *A61B 2034/303* (2016.02)

(56) References Cited

U.S. PATENT DOCUMENTS

2006/0199999 A1   9/2006   Ikeda et al.
2007/0175213 A1*  8/2007   Featherstone ........... F03G 7/065
                                                          60/527
2009/0143730 A1   6/2009   De Polo et al.

FOREIGN PATENT DOCUMENTS

JP      H04180746 A      6/1992
WO      2004/009995 A1   1/2004

OTHER PUBLICATIONS

Lai, Chih-Ming, Cheng-Yu Chu, and Chao-Chieh Lan. "A two-degrees-of-freedom miniature manipulator actuated by antagonistic shape memory alloys." Smart Materials and Structures 22.8 (2013): 085006.

Ho, Mingyen, and Jaydev P. Desai. "Modeling, characterization and control of antagonistic SMA springs for use in a neurosurgical robot." Robotics and Automation (ICRA), 2013 IEEE International Conference on. IEEE, 2013.

Intellectual Property Office Search Report for corresponding Application Serial No. GB1407490.0, dated Nov. 20, 2017, pp. 1-4.

* cited by examiner

COMPLIANT ACTUATOR

RELATED APPLICATIONS

The present application is a U.S. National Stage under 35 USC 371, claiming priority to PCT Application No. PCT/GB2015/051191 filed on Apr. 23, 2015; which claims priority to UK Application No. 1407490.0 filed Apr. 29, 2014, the entirety of both of which are incorporated herein by reference.

FIELD OF THE INVENTION

The present invention relates to the provision of an actuator driven by the elongation and contraction of shape memory alloy (SMA) wires when heated by electrical power. The actuators can find use in a wide range of products including endoscopes for medical and non-medical use and in snake-like robots (SNLRs).

BACKGROUND TO THE INVENTION

SMAs are used in small actuators because of their ability to change shape by heating, and their low weight and high force/weight ratio. Several mini actuators have been proposed using SMAs.

When the size and the forces generated required by the design increase, SMAs are used in combination with a frame or body. The expansion and contraction of the SMA component(s) drives the motion of one frame or body part relative to a base part. Most such devices use SMA wires in conjunction with a spring or springs to restore the position of the actuator after motion caused by the change in shape of the SMA components.

As an alternative to providing the restoring force by means of a spring, the use of SMA components acting antagonistically has been proposed. Pairs of SMA components such as wires or springs are arranged to provide motion in contrary directions when powered. This provides positive drive in each direction of motion, rather than relying on a restoring force for one direction.

In some proposed devices tension springs are used in an in line configuration to moderate the forces provided by the SMA components to the driven parts. For example in Smart Materials and Structures 22 (2013) 085006, Lai et al propose a miniature manipulator with two degrees of freedom provided by rotation of two links about two perpendicular axes. The rotations are each driven by pairs of antagonistic SMA wires mounted from a fixed base to the rotating part. Tension springs are fitted in series with each SMA wire, intervening between the wire and the moving part, to reduce stress on the SMA components.

When designing an actuator making use of SMA components for manipulating the direction of at least part of an endoscope, or to provide motion to a snake-like robot (SNLR), a number of issues arise. The heat generated in use of the SMA components in use must be dissipated and/or kept to an acceptable level. Other issues include the relatively small extent of motion provides by SMA wires, typically no more than 5% contraction on heat activation; and the desire for compact arrangements that can nevertheless provide complex motion.

DESCRIPTION OF THE INVENTION

According to a first aspect the present invention provides an actuator comprising:
 a moving member pivotally connected to a base unit for rotation about an axis;
 wherein the driving force for rotation of the moving member relative to the base unit is provided by a pair of antagonistically operating shape memory alloy (SMA) wires and transmitted via a torsional spring.

The advantages of using a torsional spring include that it decouples the SMA wires from the driven components resulting in a joint (between the moving member and base unit) that is flexible and compliant with stiffness depending on the selected characteristics of the spring. At the same time energy efficiency is improved thus reducing heat generated from the use of SMA components to drive the motion. Mechanical bandwidth is improved. Mechanical bandwidth is an issue for SMA powered actuators when high force or torque is required. Typical SMA systems are relatively slow, which means that the manoeuvrability of the system is reduced and the time to perform a task involving motion of the actuator is increased.

The spring also provides the benefit that an applied torque to the joint, caused by an external force, can be accepted by the torsional spring, avoiding or mitigating additional stress or even damage to either the actuator or the surroundings. This is especially important when the surroundings are delicate, e.g. the tissue of a patient undergoing internal examination using an endoscope including one or more actuators of the invention.

The actuator employs a pair of antagonistically operating SMA wires. At least two wires are required to provide the antagonistic action. In some cases, two pairs of wires or more may be employed to drive the same rotation.

The moving member is pivotally connected to the base unit for rotation about an axis. The motion of the moving member about the axis provides one degree of freedom (DoF) motion. For many applications an actuator providing two degrees of freedom or even three degrees of freedom is useful, allowing a range of more complex motion. A two degree of freedom actuator may be obtained by connecting two of the actuators together via their base units and arranging the axes (one for each actuator) to be at different angles with respect to each other. For example, at right angles with respect to each other.

Alternatively, to allow a greater range of motion, an actuator may include two moving members. Thus the actuator may comprise:
 two moving members disposed to either side of a base unit, each of the moving members being independently pivotally connected to the base unit for rotation about an axis transverse to the longitudinal axis of the actuator;
 wherein the driving force for rotation of each moving member relative to the base unit is provided by a pair of antagonistically operating shape memory alloy (SMA) wires and transmitted via a torsional spring, for each moving member.

The longitudinal axis of the actuator is an axis running in the direction from one of the moving members, through the base unit and then through the second moving member on the other side of the base unit, when the moving members and base unit are in linear or substantially linear alignment.

Advantageously, for most uses, the rotation axes of the two moving members are at right angles to each other, providing two degrees of freedom to the motion of the actuator. More advantageously the rotation axes of the moving members are at right angles to each other and intersect, to provide an arrangement that can operate as a particularly compact universal joint.

Yet further options for motion may be provided by providing an actuator with three degrees of freedom. Where two degrees of freedom are provided by two moving members having rotation axes transverse to the longitudinal axis of the actuator, the third degree of freedom is a rotation about the longitudinal axis. Only one moving member needs to have this feature to provide an actuator with three degrees of freedom. The rotation about the longitudinal axis can be powered in the same way as the rotation about the other axes. Further versatility in motion may be provided by allowing each moving member to pivot about a transverse axis and to rotate around a longitudinal axis.

Conveniently the pairs of antagonistically operating SMA wires employed in driving the motion of the actuators are mounted within the body of the actuator. For example each pair of SMA wires, or the bulk of each pair of SMA wires, is mounted in its corresponding moving member. The pair of wires can then be used to rotate a wheel or shaft driving the motion of the moving member relative to the base unit, via the torsion spring. This arrangement allows the base unit to be particularly compact, as it does not carry the bulkier mechanical components of the actuator driving system. This is especially useful where the base unit is fitted with two moving members which links the moving members together. However, the opposite arrangement, where the SMA wires or the bulk of the SMA wires are carried within the base unit may be employed. With either of these arrangements the SMA wires are carried within the body of the actuator (moving member or moving members and base unit), making the actuator suitable for uses such as endoscopes or snake-like robots (SNLR), where mechanical components external to an actuator or to a linked series of actuators is a less convenient arrangement.

SMA wires typically have a rather limited range of extension and contraction in normal use; generally up to no more than 5%-6% contraction in length is achieved. Therefore in order to achieve a useful range of motion for each moving member relatively long SMA wires are required, for example to rotate a drive shaft through a sufficient angle of rotation. Conveniently SMA wires are coiled or otherwise wound round within the body of the actuator; so as to allow fitting of sufficiently long lengths of wire for the desired degree of rotation. This can be achieved by running the SMA wires around a plurality of pulleys within the body of the actuator. e.g. within the body of the corresponding moving member as described hereafter and with reference to a specific embodiment. The use of pulleys as guides for the paths of the SMA wires reduces friction as the wires elongate and contract in use.

It is preferred that the SMA wires and associated pulleys (if employed) together with the torsion spring or springs, are mounted within the actuator body, in which case actuator body parts (moving member or moving members and base unit) may be hollow or may comprise frame structures having open space within, to allow fitting of mechanical parts such as the SMA wires, torsion springs and drive shafts or wheels. Such an arrangement also allows fitting of power supply cables and control devices as discussed further hereafter and with reference to specific embodiments. Each pair of SMA wires can be arranged to drive a wheel or shaft mounted in the actuator body. The wheel or shaft rotates on the respective rotation axis. The rotation of the wheel or shaft is transmitted to the joint between the base unit and the moving member via a torsional spring, to move the moving member with respect to the base unit.

The actuators of the invention can be of many different shapes and sizes. They can find use in medical devices such as endoscopes or in snake-like robots (SNLRs). Thus according to further aspects the present invention provides an endoscope or a shake-like robot comprising at least one of the actuators described herein.

A convenient shape for actuators of the invention is cylindrical or generally cylindrical. This is convenient, for example when the actuator is for use in, or as part of, an endoscope body or SNLR.

For example when the actuator carries two moving members on the base unit the shape is cylindrical or generally cylindrical, when the moving members and base unit are in linear or substantially linear alignment.

Thus in a convenient form the actuator body may comprise a circular or generally circular ring as a base unit.

Where only one moving member is employed, the moving member may comprise a frame having a circular or generally circular end, distal to the ring and connecting to the ring by means of two longitudinally extending connector arms which attach to diametrically opposite pivot positions on the ring.

Where the actuator body includes two moving members disposed to either side of a base unit, a base unit in the form of a circular or generally circular ring is also convenient. The moving members may be mounted axially to either side of the ring. The moving members may each comprise a frame having a circular or generally circular end, distal to the ring, and connecting to the ring by means of two longitudinally extending connector arms which attach to respective and diametrically opposite pivot positions on the ring.

For cylindrical or generally cylindrical actuators circular ends of the moving member frame or frames may be of the order of the same diameter as the ring.

The connector arms are conveniently attached at the circumference of the circular frame ends, but other designs are possible. The actuator body parts may be made of metal of plastics to suit the required duty.

Where the actuator body includes two moving members disposed to either side of a base unit, to provide two degrees of freedom of motion, as in a universal joint, the connector arms of one moving member attach to the ring at a position of 90 degrees rotation from the connector arms of the other moving member. This provides rotation axes of the moving members at right angles to each other. Advantageously the rotation axes intersect at the centre of the cylinder diameter, to allow the ring to be of minimum height and provide a compact and symmetrical cylindrical form to the actuator.

Conveniently each wire of each pair of antagonistic SMA wires is separately mounted around a pulley arrangement in the respective moving member. Each pair of wires can be arranged to drive a wheel or shaft mounted on the respective rotation axis, for example mounted on the moving member but within the body of the base unit. The rotation of the wheel or shaft is transmitted to the base unit via a torsional spring, which may be in the form of a wire engaging at one end with the wheel or shaft and the other with the base unit. The wire forming the torsional spring may be coiled or looped around the rotation axis. Other forms of torsional spring may be provided, for example a rod or bar of a resiliently flexible material that tends to twist when torque is applied.

In a further convenient example the torsional spring may be a magnetic torsional spring. The magnetic field acts to transmit the rotational motion (produced by the SMA wires) of one part, to another part. The magnetic field can be provided by a magnet or array of magnets on one part interacting with ferromagnetic material or another magnet or array of magnets on the other part. For example each pair of SMA wires can be arranged to drive a wheel or shaft mounted on the respective rotation axis, for example mounted on the moving member but within the body of the base unit. The wheel or shaft has a magnet or a circular array of magnets mounted on it. The base unit has ferromagnetic material or a magnet or array of magnets mounted close to the wheel or shaft so that there is a magnetic interaction between the wheel or shaft and the base unit. The rotation of the wheel or shaft is transmitted to the base unit via the magnetic field, giving a compliant connection. The torsional resistance is provided by the magnetic interaction.

Conveniently an array of permanent magnets is used on both parts. For example a circular array of permanent magnets about a wheel or shaft mounted on the respective rotation axis and driven by the SMA wires connects by the magnetic field to a corresponding circular array of permanent magnets mounted about the rotation axis on the base unit and near the driven wheel or shaft. Electromagnets may be used as an alternative to permanent magnets.

The actuators of the invention are driven by the elongation and contraction of antagonistic pairs of SMA wires. The wires typically may be made of NiTi alloy. The change in length of the SMA wires (contraction by heating) can be achieved by supply of electrical power in the usual way.

Conveniently, especially where a number of the actuators are employed such as in a snake-like robot or an endoscope with complex motion capability, a distributed power and control system may be employed. Four wires are run through the series of actuators. Two wires provide power supply and two a serial communication bus that may be parallel connected to each actuator joint.

Within each actuator body or attached to each actuator body a Digital Signal Processor (DSP), processes and implements a low level control, setting several parameters, such as torque, and position or force for each SMA wire. A mosfet or BJT (Bipolar Junction Transistor) or other driver circuit and current sensor can be provided to regulate the power for each SMA wire.

Further control can be located in a main control board at an end of the robot. If required high level control can be provided by an external computer for more advanced work or complex tasks.

To provide complex motion allowing an elongate device such as an endoscope or a snake-like robot to follow a tortuous or convoluted path a plurality, typically a series of several, actuators of the invention may be connected together. Where the actuator bodies include two moving members disposed to either side of a base unit, the actuators may be connected end to end. The power and control cabling may conveniently run through the actuator bodies. Alternatively the cabling may run alongside the outside of the actuator bodies. This connection to form a series of two or more actuators may be achieved in various ways.

The actuators may be joined one to the next by link pieces, for example rigid link pieces. The link pieces may be pivotally or rigidly connected to actuator bodies, for example to ends of moving members distal to the base unit.

Conveniently actuators are joined in series by attaching ends of moving members, distal to their respective base units, directly together. For example, by bonding with an adhesive, fusing together of plastics by heating, or by welding where metal components are used. Alternatively a distal end of a moving member may have connector arms that project away from its corresponding base unit for pivotal connection to the next base unit in a series.

Devices containing one or more of the actuators described herein may find use in medicine, in medical instruments such as endoscopes or devices for minimal access surgery, because of the flexibility, compliance and dexterity provided by the actuator or actuators. Actuators of the types described herein may be of different shapes sizes depending on the duty required. For applications such as an endoscope the size may be, for example of the order of 20 mm diameter by 20 mm length or even significantly smaller. They can be lightweight, weighing of the order of 1 g to 3 g or less, for example.

Many industrial activities can also make use of devices carrying one or more actuators. For example a device such as a snake-like robot can carry a camera for inspection of otherwise inaccessible spaces (e.g. pipe inspection, mechanical component inspection inside machinery).

For both medical and industrial uses tools may be carried out at the tip of an endoscope or snake-like robot.

DETAILED DESCRIPTION OF THE INVENTION WITH REFERENCE TO SOME PREFERRED EMBODIMENTS

Figure 1:
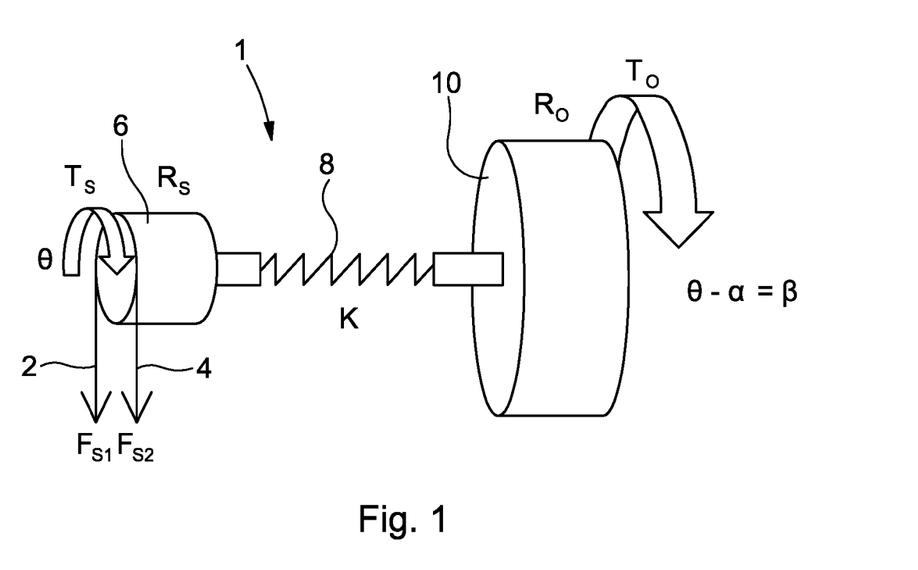
FIG. 1 illustrates schematically the operation of an actuator.

FIG. 1 shows schematically the principle of the drive mechanism 1 of an actuator of the invention. A pair of shape memory alloy (SMA) wires 2,4 act antagonistically to cause drive either clockwise or anti-clockwise to a drive wheel 6. (Power supply and control system to heat the SMA wires 2,4 not shown in this figure, see FIG. 6). As shown on the drawing a torque $T_S$ is being applied as the resultant of the forces $F_{S1}$ and $F_{S2}$. The torque is transmitted via torsional spring 8 to provide output torque $T_O$, and hence motion, to a joint represented by wheel 10 in the schematic of the figure.

The working principle is showed in FIG. 1 and equation 1 below describes the statics, Where it is assumed that $T_O = T_S$:

$$(F_{S2} - F_{S1})R_S = \tau_S = K\alpha = -\tau_O \quad (1)$$

$$K = \frac{-\tau_O}{\alpha_{MAX}} = \frac{\tau_S}{\alpha_{MAX}} \quad (2)$$

where $F_{S1}$ and $F_{S2}$ are the forces provided by each SMA, $T_S$ is the resultant torque, K the torsional spring elastic constant, $R_S$ the radius of the SMA pulley, $R_O$ is half of the joint length (radius of the wheel representing the joint), θ the angle of the SMA pulley, α the angle of the torsional spring, $\alpha_{MAX}$ the max compliance angle. Eq. 2 provides a definition of K used to design the torsional spring.

An SMA provides a residual force of about $F_{MAX}/3$, where $F_{MAX}$ is the maximal contracting force, which implies a residual torque of $T_S/3$, when the power supply is off. The resultant force provided by SMA wires in antagonistic configuration is as follows:

$$F_S = F_{MAX} - \frac{1}{3}F_{MAX} = \frac{2}{3}F_{MAX}$$

This allows the joint to have a residual compliance of $\alpha_{MAX}/3$. Each joint can provide an output torque $T_O$ as described by the following equation:

$$\left(\frac{2}{3}F_{MAX}\right)R_S = \tau_{MAX}$$

which is reduced by about ⅓ due to the residual strain of the opposite antagonistic SMA wire when it is not powered. The residual torque can be adjusted by controlling the temperature of the SMA, resulting in increased joint stiffness.

By decoupling the input torque $T_S$ produced by the SMA wires 2,4 from the output torque $T_O$, the joint has increased efficiency, and hence reduced heat generation. At the same time the joint is compliant, the motion to a particular position is not rigid but flexible to the extent dictated by the torsional spring 8. Furthermore if an actuator containing the drive 1 is acted upon by an external force, distortion of the torsional spring 8 will allow compliance of the joint direction in response to the amount of force encountered. For example, if the actuator is a component of an endoscope encountering a bend in the wall of a passage.

Figure 2A:
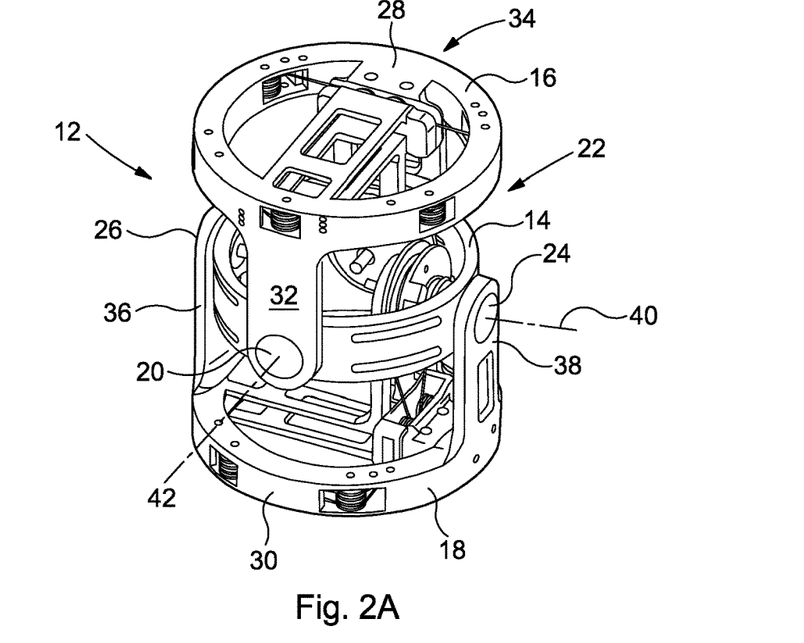
FIGS. 2A to 2C illustrate actuators.

FIG. 2A shows an actuator 12 of cylindrical form comprising three main body parts. A base unit 14 in the general form of a ring has two moving members 16,18 connected to it at respective pairs of pivot points 20,22 and 24,26. The moving members comprise frames for carrying mechanical and electrical components. Each moving member 16,18 has distal circular ends 28,30 that connect to the base unit 14 by means of respective pairs longitudinally extending connector arms (32,34 and 36,38) which attach to respective and diametrically opposite pivot points on the base unit 14 ring.

Figure 2B:
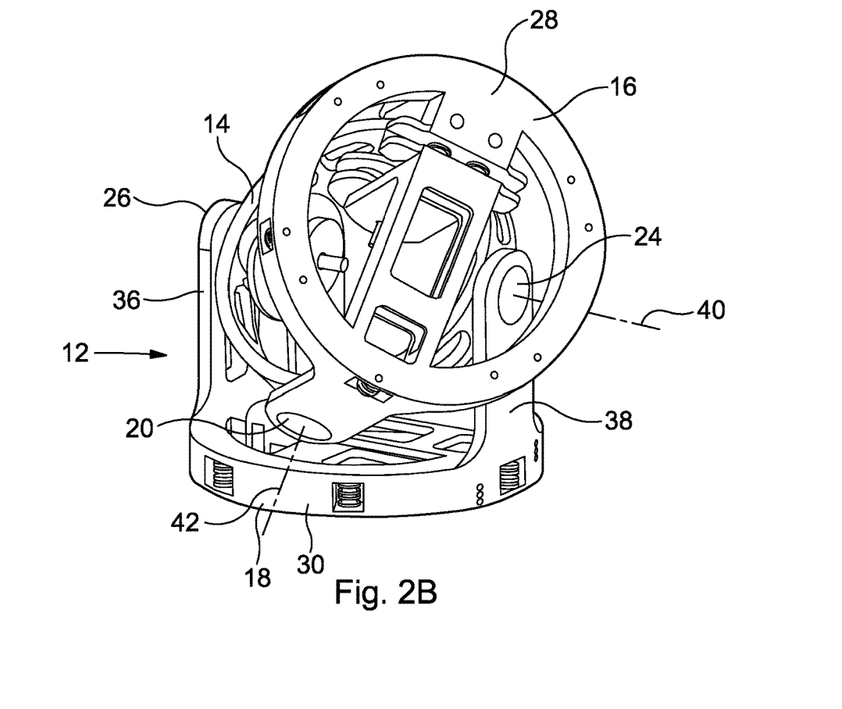

The arrangement depicted in FIG. 2A has rotation axes 40,42 at right angles and intersecting at the centre of the base unit, providing a compact form of universal joint with two degrees of freedom allowing both pitch and roll motion as illustrated by FIG. 2B, which shows the actuator 12 of FIG. 2A tilted about both rotation axes.

Figure 2C:
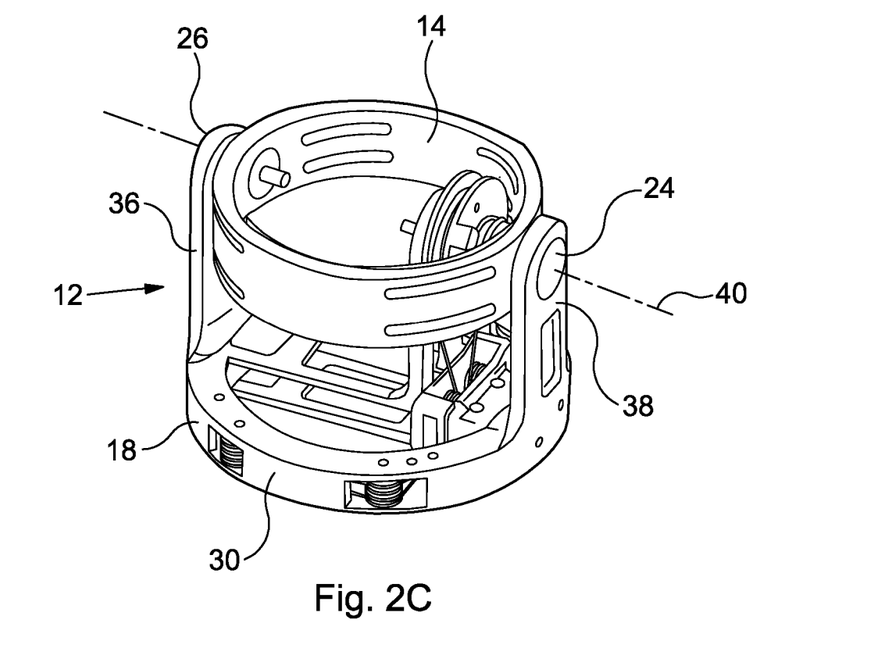

FIG. 2C shows an actuator 12 of cylindrical form and similar to that of FIGS. 2A and 2B but comprising only two main body parts, moving member 18 and base unit 14. Like parts are numbered the same. This actuator 12 provides only one degree of freedom (one axis of rotation). However, joining together with another of the same type base unit 14 to base unit 14, can provide a two degree of freedom actuator if the rotation axes are arranged to be e.g. at right angles as in the arrangement of FIGS. 2A and 2B.

The drive mechanism employed to cause motion between the moving member 18 (FIG. 2C) or moving members 16,18 (FIGS. 2A, 2B) and base unit 14 is more easily with reference to FIG. 3.

Figures 3A, 3B, 3C:
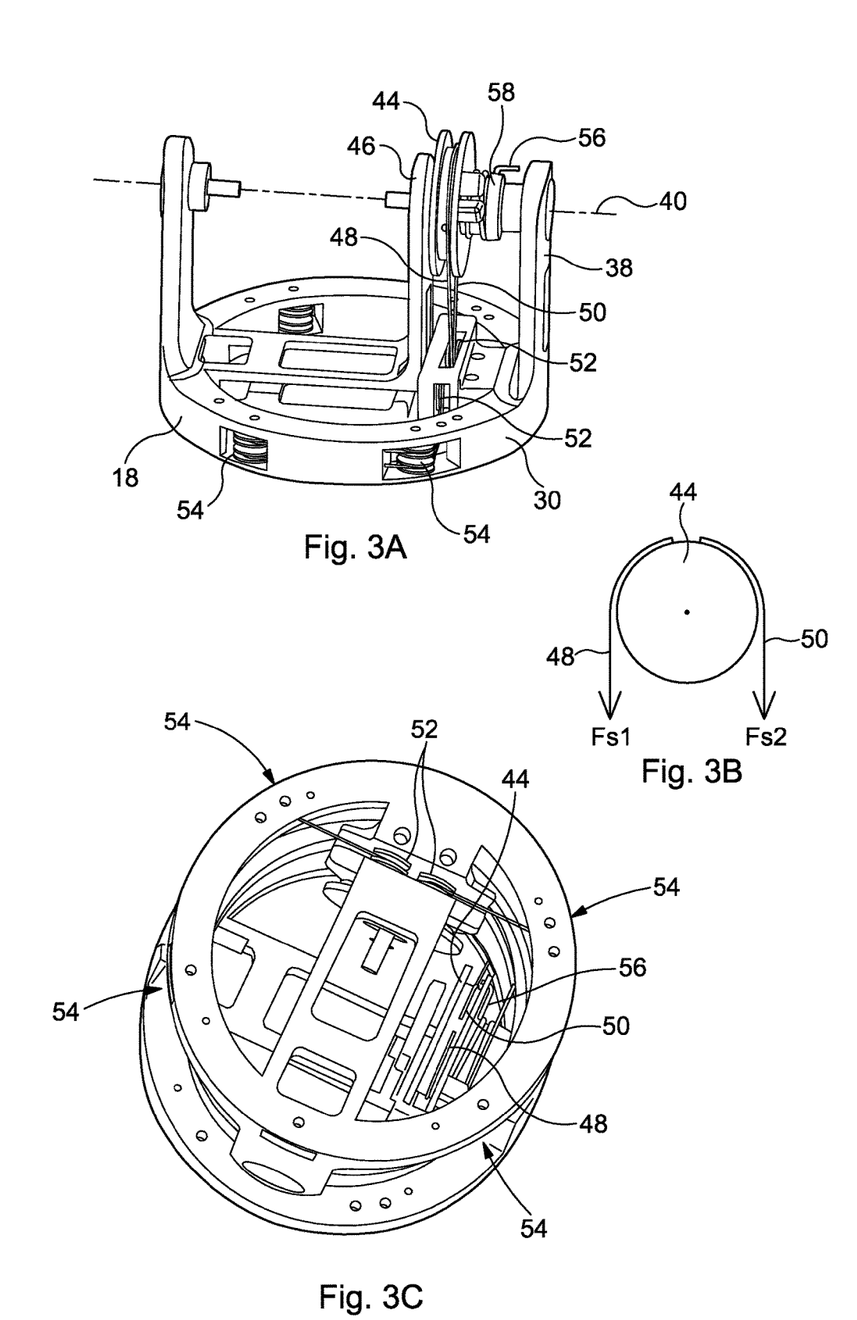
FIGS. 3A to 3E illustrate aspects of actuators.

FIG. 3A shows a moving member 18. A drive wheel 44 is mounted between a connector arm 38 and a drive wheel support arm 46 for rotation about rotation axis 40. Rotation of the drive wheel 44 is driven by a pair of shape memory alloy (SMA) wires 48,50 acting antagonistically on the wheel 44 as indicated by arrows $F_{S1}$ and $F_{S2}$ as depicted in schematic FIG. 3B showing drive wheel 44 viewed looking along axis 40. The arrows suggest the applied force generated by activation of one or both wires by their power supply (not shown). Power supply may conveniently be provided by a single common power connection to drive wheel 44 for the ends of both SMA wires 48, 50 and a further connector wire for each SMA wire to complete the circuits.

Long lengths of SMA wire are accommodated in the moving member 18 by running each wire 48, 50 around a series of pulleys. In this example each wire is guided from the drive wheel 44 by a respective pulley 52 in the distal end 28 of the moving member, to then run around two further pairs of pulleys 54. The pulleys 52 can be more easily seen in the view from below of the actuator 12 of FIG. 2A, as shown in FIG. 3C.

FIG. 3C also shows one of the ends of each SMA wire 48 and 50 on a drive wheel 44. After wrapping round pulleys 52 and 54 an SMA wire may have its other end terminating at one of the pulleys 54 or by attaching to the moving member carrying the pulleys.

Pulleys 54 are conveniently located in the end 30 of the moving member. Coiling longer lengths of wire within the actuator body in this fashion allows greater motion to be achieved on activation of the SMA wires. Typically only up to 5% contraction of the wire length is achievable.

Figure 3D:
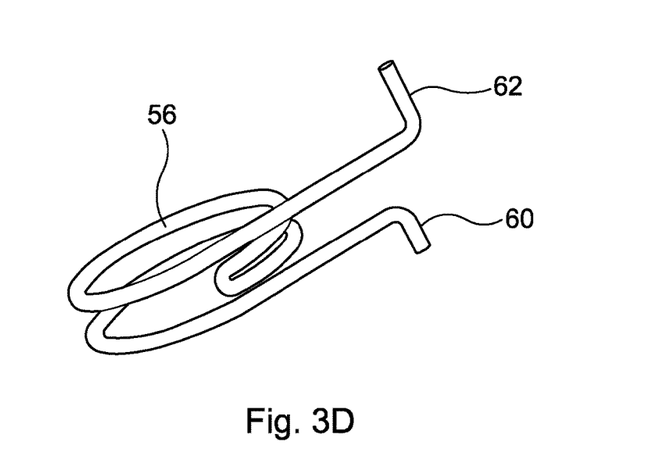
Figure 3E:
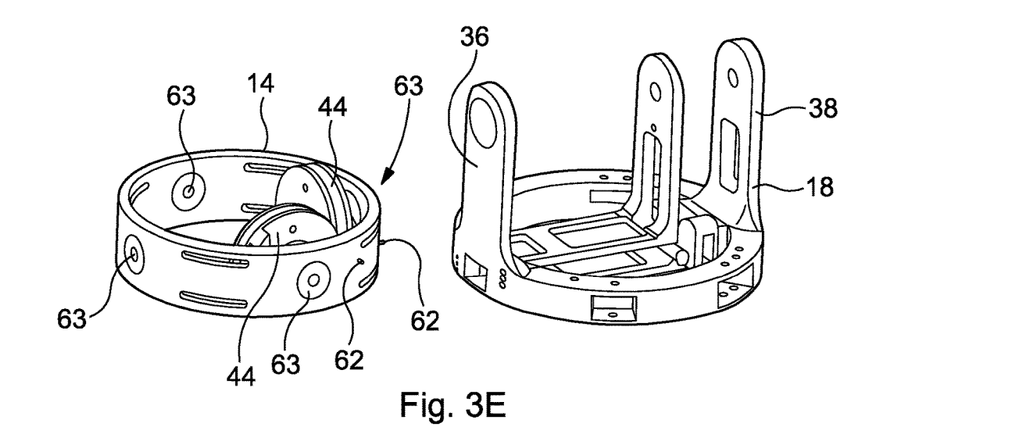

The drive from wheel 44 is transmitted to the base unit 14 via torsional spring 56 of a suitable material which may be metal such as steel or of a plastic or polymer composition. Spring 56 acts along the axis 40. The spring 56 in this example wraps around a bushing 58 of wheel 44. As shown in FIG. 3D the spring 56 has two ends 60, 62. In use one end 60 fits into an aperture on wheel 44, the other 62 into an aperture in base unit 14 (see FIG. 3E). Thus action of the SMA wires 48,50 driving the wheel 44 is transmitted to move the moving body 28 relative to the base unit 14. FIG. 3E also shows mounts 63 for ball bearings (not shown) at the pivot points of base unit 14. These allow smooth and reduced friction pivoting of a moving member 18 when attached by its connector arms 36,38.

The arrangement shown is advantageous. The drive wheel 44 is controlled by the two SMA wires in antagonist configuration and it fixes the equilibrium point of the system, which is a stable configuration of the system if no external force is applied. The equilibrium point can be controlled even if an external torque is applied because the two SMA wires are directly connected to the wheel 44. If an external torque is supplied, the drive wheel 44 will tend to stay in the chosen equilibrium point, even though the moving member may move—the torsion spring allows motion of the moving member without disturbing the drive wheel. In the prior art systems using springs in tension, each SMA wire has a serialised spring that does not allow a fixed equilibrium position. If an external torque is applied, one spring is compressed and the other stretched. In contrast, with actuators as described herein, the equilibrium position of the drive wheel can be accurately controlled. Control of the drive wheel position can be for example by embedding a sensor in the wheel 44 to determine the position and adjustments made by powering the SMA wires. The position of the drive wheel 44 can also be determined for control purposes by measuring the length of the SMA wires. The length of an SMA wire can be determined by measuring the resistance of the wire, which varies with the length.

Figure 4A:
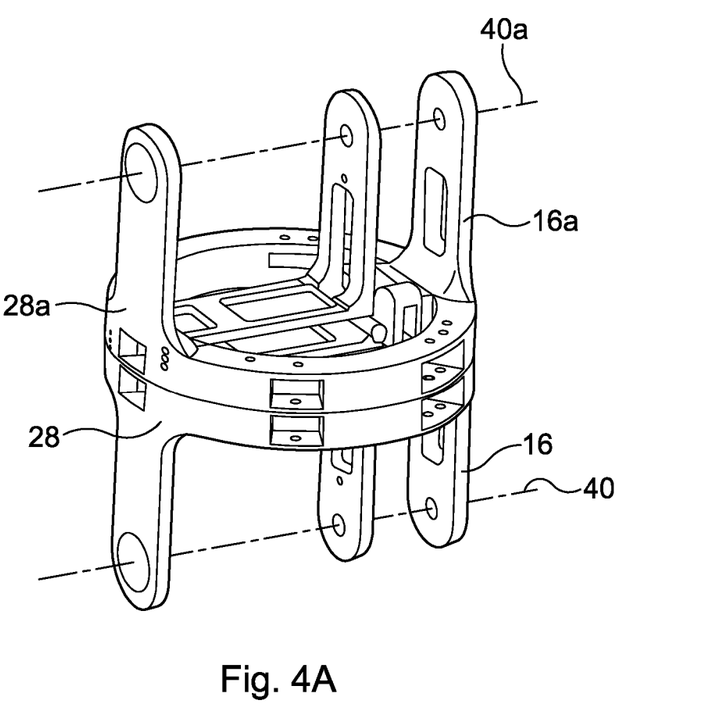
FIGS. 4A to 4D illustrate alternative moving members for actuators.
Figure 4B:
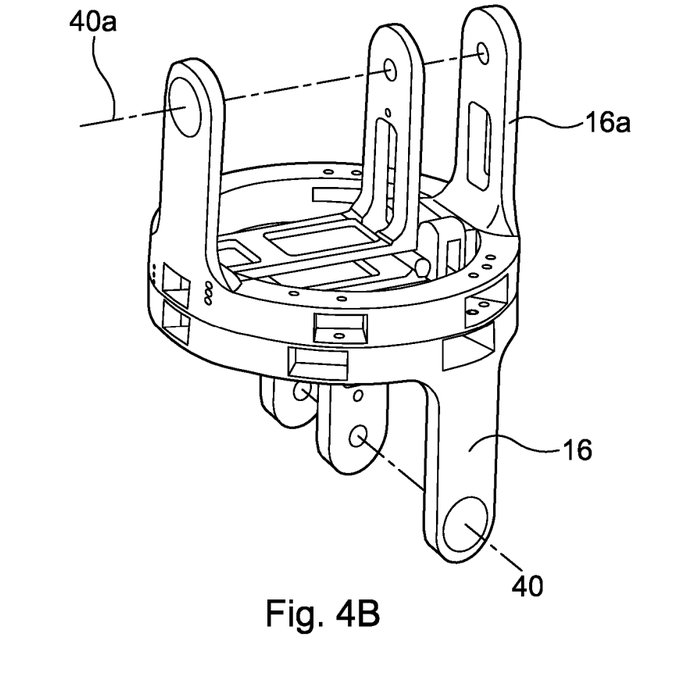
Figure 4C:
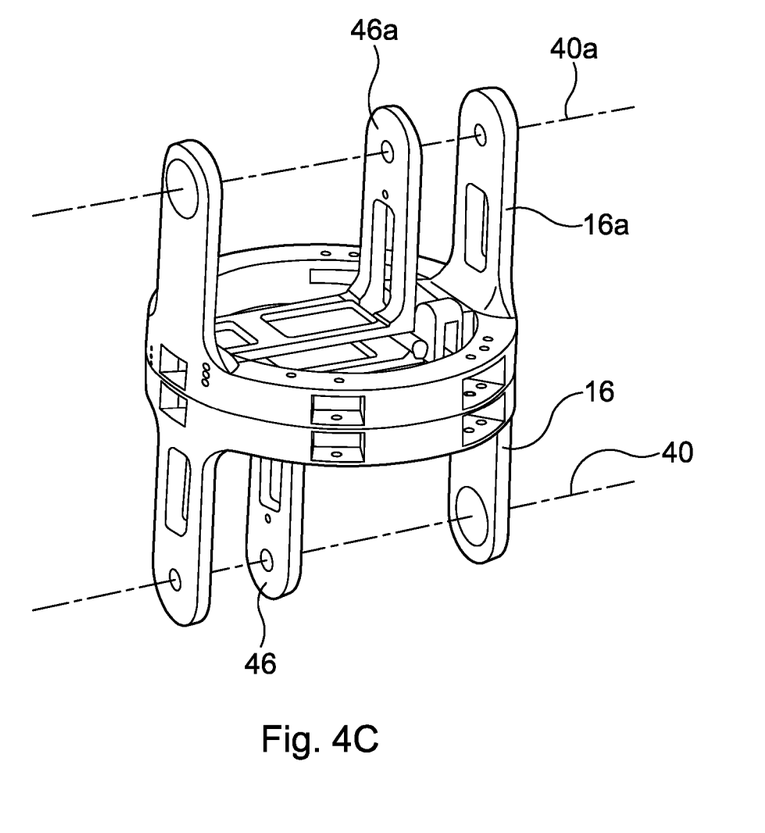
Figure 4D:
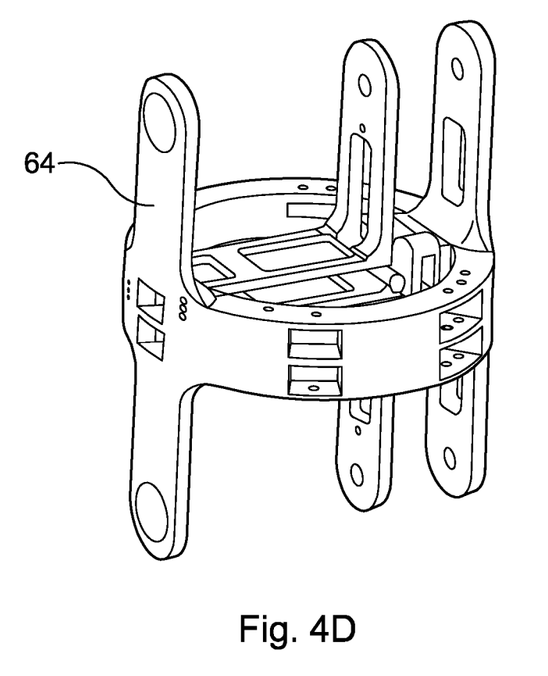

FIG. 4A shows two moving members 16, 16a bonded end 28 to end 28a. Only the frame part of each moving member and not components carried within are shown in this illustration for clarity. This arrangement allows actuators such as shown in FIG. 2 to be connected directly one to another to provide two or more actuators linked together in series. The angle between the rotation axis 40 of one moving member and that of the next (40a) may be varied about the longitudinal axis as shown in the examples of FIGS. 4B and 4C. In FIG. 4C the support arms 46, 46a are opposed so that drive wheels 44 (not shown here, see FIG. 3A), when fitted to their respective moving members, are radially opposite, Such arrangements can be more convenient for routing of power and control cables and the placing of electronic components within the actuator bodies, and/or to balance the forces exerted on operating the series of actuators.

As an alternative to bonding together two separate components 16,16a as shown in FIG. 4 a single component 64 may be manufactured having the same general form of the bonded together pair shown in FIG. 4A. See FIG. 4D. This can be convenient in manufacture, where a series of actuators are required, e.g. in building a snake-like robot. One moving body 64 connects between two base units in the series.

Figure 5:
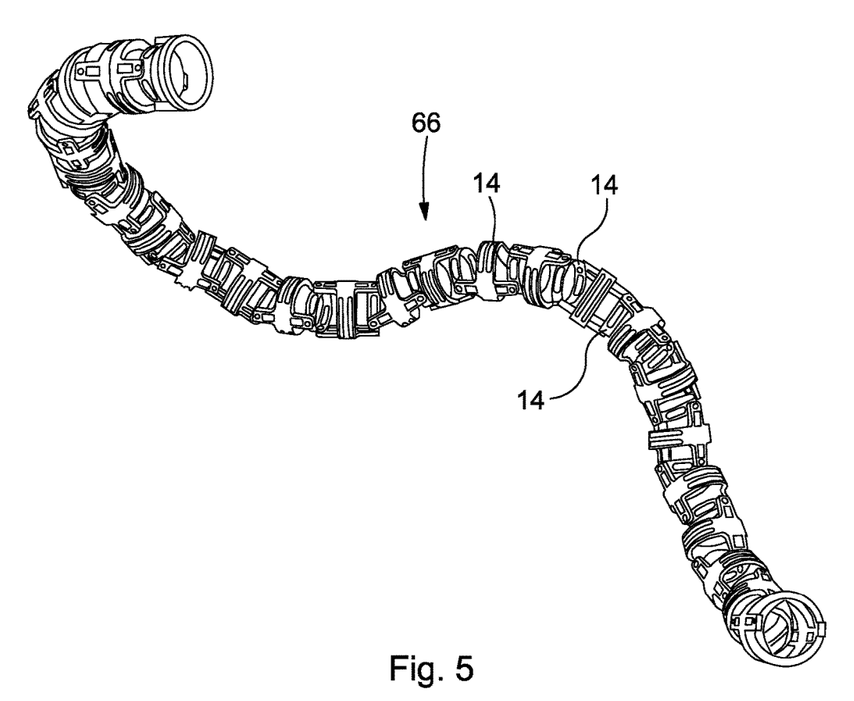
FIG. 5 illustrates schematically a snake-like robot.

FIG. 5 shows a schematic view of a snake-like robot (SNLR) 66 comprising a series of actuators of the invention mounted end to end resulting in an articulated "snake". The SNLR is capable of adopting relatively complex shapes and thus can be suitable for exploring convoluted narrow channels such as a human colon when used as an endoscope. In this example pairs of moving members 16,16a bonded together as in FIG. 4A or a single component 64 having two pairs of connector arms as in FIG. 4D may be employed to link base units 14 together in making up the SNLR.

Figure 6:
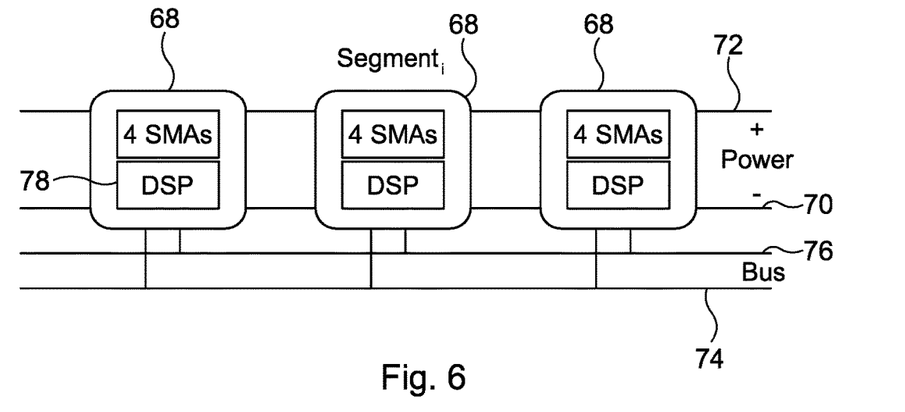
FIG. 6 illustrates schematically a power and control system.

FIG. 6 shows schematically an arrangement for powering and controlling a series of connected actuators of the invention. Such an arrangement may be found in an endoscope employing several actuators for improved range of motion, or more generally in a snake-like robot. In the figure three segments 68 of a distributed power and control system are shown. Each segment is located in an actuator such as those shown in the preceding figures. Each independent segment embeds all the required hardware to control the two degrees of freedom motion of its corresponding actuator.

In order to achieve this requirement, the electronic system relies on a distributed system using a parallel bus to exchange control data. Four wires are needed for the actuators: two providing power supply 70, 72, and two 74,76 for the serial communication bus. A digital signal processor (DSP) 78, processes and implements a low level control, setting several parameters, such as torque, position or force for each of the four SMA wires. Four mosfets and current sensors will regulate the power for each SMA wire.

Further control, a mid-level control (not shown), can be located in a main control board at the end of the robot or endoscope, whereas high level control can be provided by an external PC connected to the control system shown, for more advanced computational work.

Figure 7A:
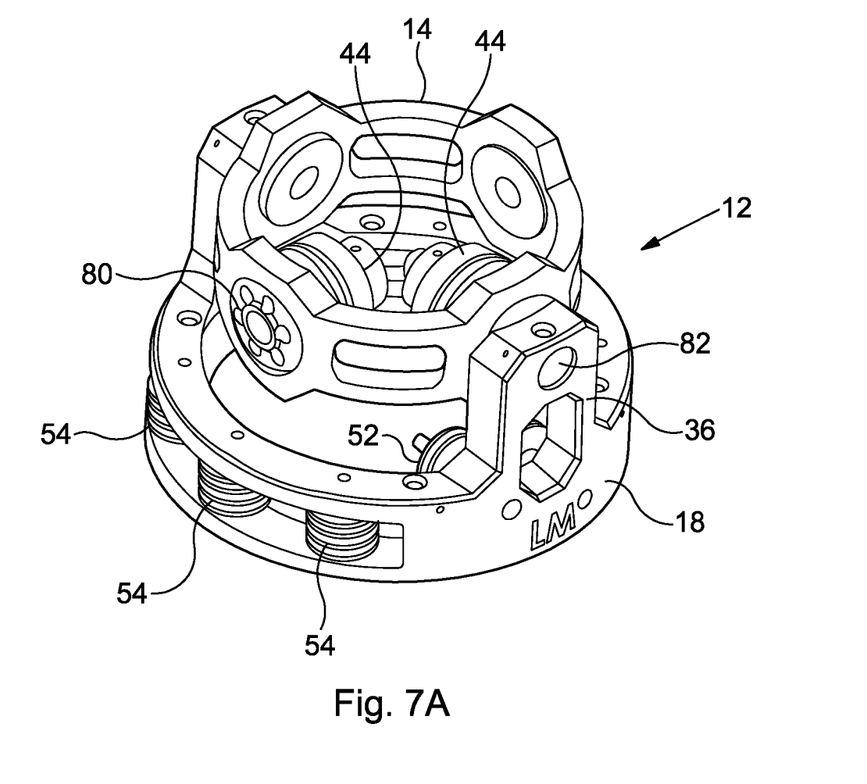
FIGS. 7A and 7B illustrate alternative aspects of actuators.
Figure 7B:
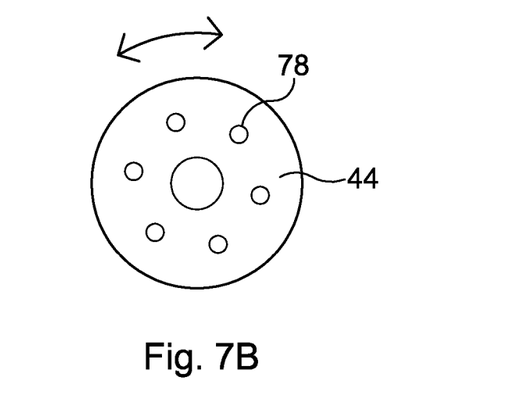

FIG. 7A shows in partial schematic view part of an actuator 12 generally similar to that of FIG. 2A but employing a magnetic torsional spring. Only one moving member 18 is shown fitted to the base unit 14 to allow better viewing of the drive details and other details are omitted. In this embodiment the drive wheels 44 are powered by pairs of SMA wires (not shown, see FIG. 3A) that wind round pulleys 52, 54. The drive wheels 44 have an array of permanent magnets 78 mounted to the outward facing face. See schematic elevation detail of a drive wheel 44 in FIG. 7B. A corresponding array of permanent magnets 80 is mounted about the rotation axis on the base unit 14, for each drive wheel 44. The drive wheel 44 is rotated by the SMA wires, in one direction or the other, as suggested by the double headed arrow in FIG. 7B. The magnetic field between the permanent magnets 78 and 80 acts to produce movement of the moving member 18 relative to the base unit 14. In this example the drive wheels 44 are fitted on shafts 82 on the rotation axes and mounted on the support arms 36 of the moving member. This example does not make use a drive wheel support arm such as shown (part 46) in FIG. 3A.

The invention claimed is:

1. An actuator comprising:
   a moving member pivotally connected to a base unit for rotation about an axis;
   wherein the driving force for rotation of the moving member relative to the base unit is provided by a pair of antagonistically operating shape memory alloy (SMA) wires and transmitted via a torsional spring.

2. The actuator of claim 1 wherein the pair of antagonistically operating SMA wires are mounted within the body of the actuator.

3. The actuator of claim 2 wherein the pair of antagonistically operating SMA wires or the bulk of the pair of antagonistically operating SMA wires are mounted within the moving member.

4. The actuator of claim 2 wherein the pair of antagonistically operating SMA wires or the bulk of the pair of antagonistically operating SMA wires are mounted within the base unit.

5. The actuator of claim 1 wherein the pair of antagonistically operating SMA wires are coiled or wound round within the body of the actuator.

6. The actuator of claim 5 wherein the pair of antagonistically operating SMA wires run around a plurality of pulleys within the body of the actuator.

7. The actuator of claim 6 wherein the pair of antagonistically operating SMA wires run around a plurality of pulleys mounted within the body of the moving member.

8. The actuator of claim 1 wherein the moving member and base unit are hollow or comprise frame structures having open space within.

9. The actuator of claim 1 wherein the pair of SMA wires drives a wheel or shaft mounted in the actuator body and rotating on the rotation axis; and
   wherein the rotation of the wheel or shaft is transmitted to the joint between the base unit and the moving member via the torsional spring.

10. The actuator of claim 9 wherein the torsional spring is in the form of a wire engaging at one end with the wheel or shaft and the other with the base unit.

11. The actuator of claim 1 wherein the torsional spring is coiled or looped around the rotation axis.

12. The actuator of claim 1 wherein the torsional spring is a rod or bar of a resiliently flexible material that twists as torque is applied.

13. The actuator of claim 1 wherein the torsional spring is a magnetic torsional spring.

14. The actuator of claim 13 wherein the magnetic torsional spring comprises a circular array of permanent magnets is mounted on the wheel or shaft driven by the SMA wires and a corresponding circular array of permanent magnets is mounted about the rotation axis on the base unit.

15. The actuator of claim 1 wherein the actuator body is cylindrical or generally cylindrical.

16. The actuator of claim 1 wherein the base unit comprises a circular or generally circular ring.

17. The actuator of claim 16 wherein the moving member comprises a frame having a circular or generally circular end, distal to the ring and connecting to the ring by means of two longitudinally extending connector arms which attach to diametrically opposite pivot positions on the ring.

18. The actuator of claim 1 wherein the SMA wires comprise an NiTi alloy.

19. The actuator of claim 1 wherein a distributed power and control system is employed.

20. The actuator of claim 1 comprising two moving members.

21. The actuator of claim 20 wherein the two moving members are disposed to either side of the base unit, each of the moving members being independently pivotally connected to the base unit for rotation about an axis transverse to the longitudinal axis of the actuator; and wherein the driving force for rotation of each moving member relative to the base unit is provided by a pair of antagonistically operating shape memory alloy (SMA) wires and transmitted via a torsional spring, for each moving member.

22. The actuator of claim 21 wherein the rotation axes of the two moving members are at right angles to each other, providing two degrees of freedom to the motion of the actuator.

23. The actuator of claim 21 wherein the rotation axes of the moving members are at right angles to each other and intersect.

24. The actuator of claim 21 wherein one moving member is pivotally connected to the base unit for rotation about the longitudinal axis and the rotation relative to the base unit is driven by means of a further pair of antagonistically operating shape memory alloy (SMA) wires and transmitted via a torsional spring.

25. The actuator of claim 24 wherein both moving members are pivotally connected to the base unit for rotation about the longitudinal axis and for each moving member the rotation relative to the base unit is driven by means of a further pair of antagonistically operating shape memory alloy (SMA) wires and transmitted via a torsional spring.

26. The actuator of claim 1 wherein an end of a moving member distal to the base unit has connector arms that project away from the base unit, for pivotal connection to another base unit.

27. An endoscope or a snake-like robot comprising at least one actuators;

the actuator comprising a moving member pivotally connected to a base unit for rotation about an axis;

wherein the driving force for rotation of the moving member relative to the base unit is provided by a pair of antagonistically operating shape memory alloy (SMA) wires and transmitted via a torsional spring.

28. An endoscope or a snake-like robot comprising a plurality of actuators, connected together;

each actuator of the plurality of actuators comprising a moving member pivotally connected to a base unit for rotation about an axis;

wherein the driving force for rotation of the moving member relative to the base unit is provided by a pair of antagonistically operating shape memory alloy (SMA) wires and transmitted via a torsional spring.

29. An endoscope or a snake-like robot according to claim 28 wherein the plurality of actuators are joined one to the next by link pieces.

30. An endoscope or a snake-like robot according to claim 28 wherein the plurality of actuators are joined one to the next by attaching ends of moving members, distal to their respective base units, directly together.

* * * * *